US00PP37700P2

(12) United States Plant Patent
Verduin

(10) Patent No.: US PP37,700 P2
(45) Date of Patent: Sep. 15, 2026

(54) ***ASTILBE* PLANT NAMED 'Philoselmo'**

(50) Latin Name: *Astilbe chinensis*
Varietal Denomination: Philoselmo

(71) Applicant: Harrie Verduin, Heemskerk (NL)

(72) Inventor: Harrie Verduin, Heemskerk (NL)

(73) Assignee: PHILOS B.V., Lisse (NL)

( * ) Notice: Subject to any disclaimer, the term of this patent is extended or adjusted under 35 U.S.C. 154(b) by 0 days.

(21) Appl. No.: 19/549,898

(22) Filed: Feb. 25, 2026

(51) Int. Cl.
*A01H 5/02* (2018.01)
*A01H 6/80* (2018.01)

(52) U.S. Cl.
USPC ..... Plt./407
CPC ..... *A01H 6/80* (2018.05)

(58) Field of Classification Search
USPC ..... Plt./407
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Astilbe* plant named 'Philoselmo', characterized by its broadly upright plant habit with upright inflorescences; moderately vigorous growth habit; dark green-colored leaves; early, freely and uniformly flowering habit; long flowering period; dense inflorescences; purplish red-colored flowers on strong peduncles; and good container and garden performance.

3 Drawing Sheets

Figure 1:
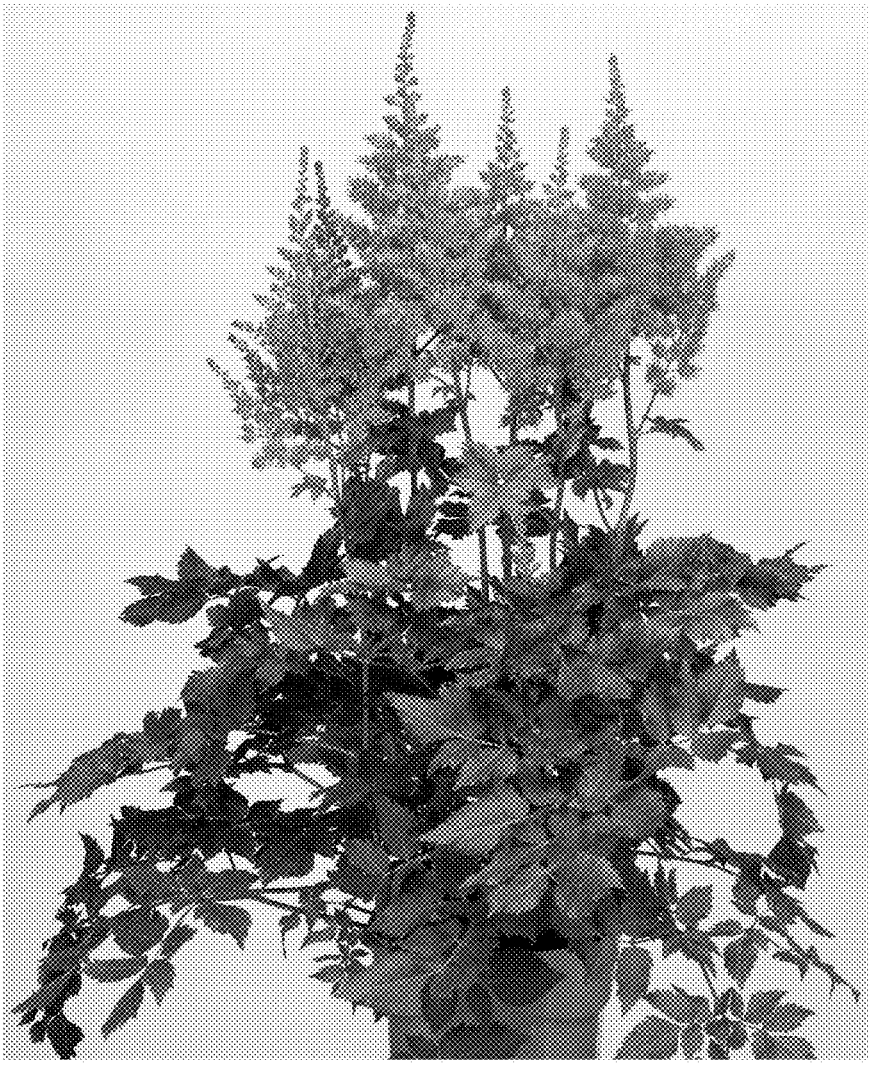

Botanical designation: *Astilbe chinensis.*
Cultivar denomination: 'PHILOSELMO'.

BACKGROUND OF THE INVENTION

The present invention relates to a new and distinct cultivar of *Astilbe*, botanically known as *Astilbe chinensis* and hereinafter referred to by the name 'Philoselmo'.

The new *Astilbe* plant is a product of a planned breeding program conducted by the Inventor in Heemskerk, The Netherlands. The objective of the breeding program was to create new fast-growing, compact, uniform and freely flowering *Astilbe* plants with attractive leaf and flower coloration.

The new *Astilbe* plant originated from a cross-pollination in 2020 in Heemskerk, The Netherlands, of two unidentified seedling selections of *Astilbe chinensis*, not patented. The new *Astilbe* plant was discovered and selected by the Inventor as a single flowering plant from within the progeny of the stated cross-pollination in a controlled greenhouse environment in Heemskerk, The Netherlands in June, 2022.

Asexual reproduction of the new *Astilbe* plant by vegetative divisions in a controlled nursery environment in Heemskerk, The Netherlands since February, 2023, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Philoselmo'. These characteristics in combination distinguish 'Philoselmo' as a new and distinct *Astilbe* plant:

1. Broadly upright plant habit with upright inflorescences.
2. Moderately vigorous growth habit.
3. Dark green-colored leaves.
4. Early, freely and uniformly flowering habit.
5. Long flowering period.
6. Dense inflorescences.
7. Purplish red-colored flowers on strong peduncles.
8. Good container and garden performance.

Plants of the new *Astilbe* differ primarily from plants of the female parent selection in the following characteristics:

1. Plants of the new *Astilbe* are more compact than plants of the female parent selection.
2. Plants of the new *Astilbe* flower earlier than plants of the female parent selection.

Plants of the new *Astilbe* differ primarily from plants of the male parent selection in the following characteristics:

1. Plants of the new *Astilbe* are more compact than plants of the male parent selection.
2. Plants of the new *Astilbe* flower earlier than plants of the male parent selection.

Plants of the new *Astilbe* can be compared to plants of *Astilbe chinensis* 'Vision in Red', disclosed in U.S. Plant Pat. No. 11,965. In side-by-side comparisons, plants of the new *Astilbe* and 'Vision in Red' differ primarily in the following characteristics:

1. Plants of the new *Astilbe* are more compact than plants of 'Vision in Red'.
2. Plants of the new *Astilbe* flower earlier than plants of 'Vision in Red'.

Plants of the new *Astilbe* can also be compared to plants of *Astilbe chinensis* 'Harvandermeerrubyred', disclosed in U.S. Plant Pat. No. 31,439. In side-by-side comparisons, plants of the new *Astilbe* and 'Harvandermeerrubyred' differ primarily in the following characteristics:

1. Plants of the new *Astilbe* are more compact than plants of 'Harvandermeerrubyred'.

2. Plants of the new *Astilbe* flower earlier than plants of 'Harvandermeerrubyred'.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1) is a side perspective view of a typical flowering plant of 'Philoselmo' grown in a container.

Figure 2:
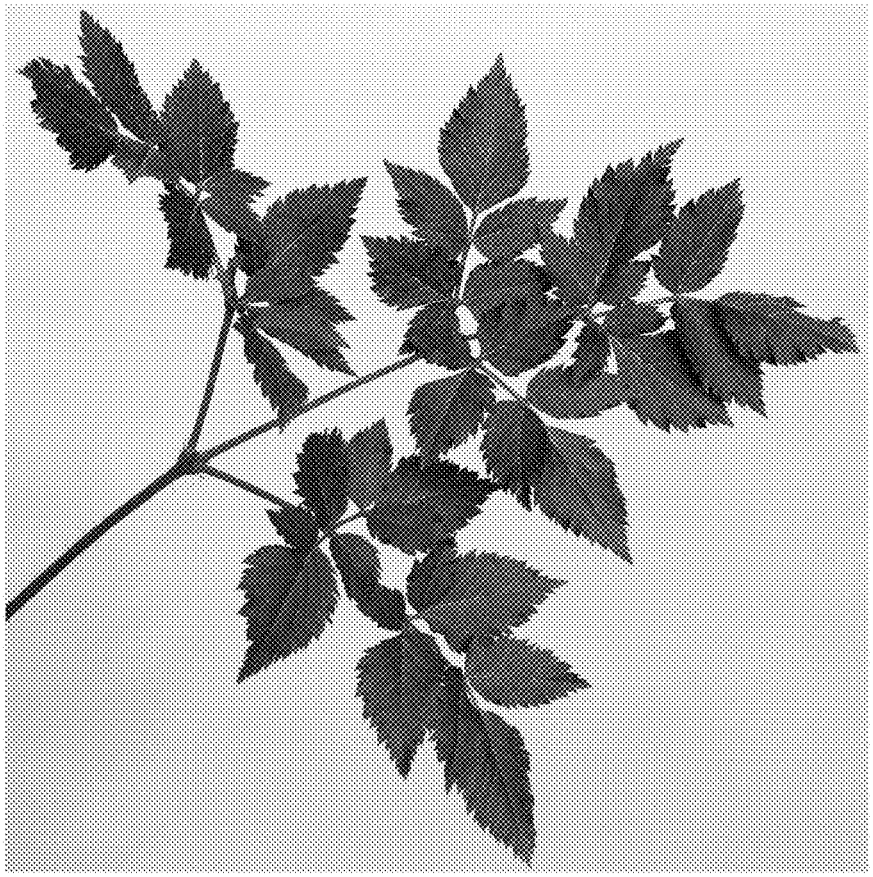

The photograph on the second sheet (FIG. 2) is a close-up view of a typical leaf and leaflets of 'Philoselmo'.

Figure 3:
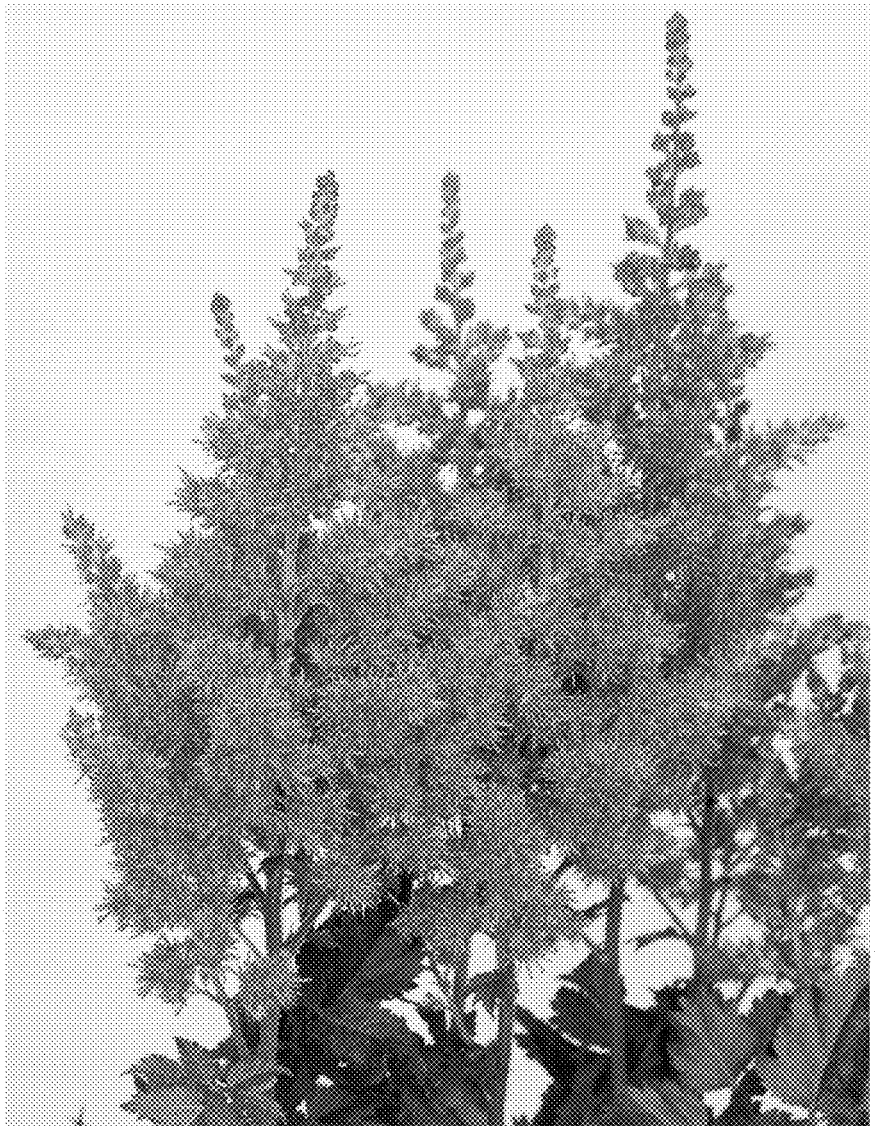

The photograph on the third sheet (FIG. 3) is a close-up view of typical inflorescences of 'Philoselmo'.

DETAILED BOTANICAL DESCRIPTION

The aforementioned photographs and following observations, measurements and values describe plants grown during the late summer and early autumn in 14.5-cm containers in an outdoor nursery in Heemskerk, The Netherlands and under cultural practices typical of commercial *Astilbe* production. During the production of the plants, day temperatures ranged from 18° C. to 32° C. and night temperatures ranged from 10° C. to 20° C. Plants were two years old when the photographs and description were taken. In the following description, color references are made to The Royal Horticultural Society Colour Chart, Sixth Edition, 2019 reprint, except where general terms of ordinary dictionary significance are used.

Botanical classification: *Astilbe chinensis* 'Philoselmo'.

Parentage:

*Female, or seed, parent*.—Unidentified seedling selection of *Astilbe chinensis*, not patented.

*Male, or pollen, parent*.—Unidentified seedling selection of *Astilbe chinensis*, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; broadly upright plant habit, overall plant shape, flattened globular, with inflorescences held above the foliar plane on upright and strong peduncles; flowering stems and leaves basal; freely flowering with numerous basal branches developing per plant, dense and bushy appearance; moderately vigorous growth habit; and early, freely and uniformly flowering habit.

*Growth rate*.—Moderately rapid; from divisions, about three months are required to produce fully-grown flowering plants in containers.

*Plant height* (*soil level to top of foliar plane*).—About 31.9 cm.

*Plant height* (*soil level to top of inflorescences*).—About 52.4 cm.

*Plant width* (*spread*).—About 52 cm.

*Stem description*.—Quantity per plant: About seven basal branches per plant. Length: About 24 cm. Diameter: About 4 mm. Internode length: About 2.5 cm. Strength: Strong. Aspect: Erect to about 10° from vertical. Texture and luster: Moderately pubescent; pubescence minute; slightly glossy. Color, developing: Close to 145A. Color, developed: Close to a blend of 144A and 146B.

Leaf description:

*Arrangement*.—Alternate; biternately compound; on average, about 41 leaflets per leaf.

*Leaf length* (*excluding petiole*).—About 20.7 cm.

*Leaf width*.—About 20.3 cm.

*Terminal leaflet length*.—About 5.2 cm.

*Terminal leaflet width*.—About 3.3 cm.

*Lateral leaflet length*.—About 3.7 cm.

*Lateral leaflet width*.—About 2.2 cm.

*Leaf shape, in outline*.—Broadly deltoid to broadly rhomboidal.

*Leaflet shape*.—Ovate to broadly ovate.

*Leaflet apex*.—Acute to apiculate.

*Leaflet base*.—Attenuate with obtuse tendencies.

*Leaflet margin*.—Biserrate.

*Leaflet texture and luster, upper and lower surfaces*.—Moderate to dense pubescence along the midvein and lateral venation; slightly glossy.

*Leaflet venation pattern*.—Pinnate.

*Leaflet color*.—Developing leaflets, upper surface: Close to 143A. Developing leaflets, lower surface: Close to a blend of 143B and 146B. Fully expanded leaflets, upper surface: Close to a blend of NN137A and 147A; venation, close to 144A. Fully expanded leaflets, lower surface: Close to a blend of 137B and 147B; venation, close to 145A.

*Leaf petiole length*.—About 11.6 cm.

*Leaf petiole diameter*.—About 3 mm.

*Leaf and leaflet petiole strength*.—Strong.

*Leaf and leaflet petiole texture and luster, upper and lower surfaces*.—Moderately to densely pubescent; moderately glossy.

*Leaf and leaflet petiole color, upper surface*.—Close to 146A and 146B; at the leaflet nodes, tinged with close to 143A.

*Leaf and leaflet petiole color, lower surface*.—Close to 144A; at the leaflet nodes, tinged with close to 143B.

*Stipules*.—Quantity and arrangement: Two, opposite, at the base of each leaf. Length: About 7 mm. Width: About 1.5 mm. Shape: Lanceolate. Apex: Narrowly acute. Base: Cuneate. Texture, upper and lower surfaces: Smooth, glabrous. Color, upper and lower surfaces: Close to 165A.

Flower description:

*Flower type and flowering habit*.—Single rotate flowers arranged on mostly upright compound panicles; flowers face upright, outward or downward depending on position on the inflorescence; panicles conical in shape; early, freely and uniformly flowering habit with about 1,200 flowers developing per inflorescence and about 8,400 flowers developing per plant during the flowering season.

*Fragrance*.—Faintly fragrant; sweet and pleasant.

*Natural flowering season*.—Plants flower continuously from the late spring until the late summer in The Netherlands.

*Postproduction longevity*.—Individual flowers last about ten days on the plant; flowers not persistent.

*Flower buds*.—Height: About 2 mm. Diameter: About 2 mm. Shape: Globular. Texture and luster: Smooth, glabrous; matte. Color: Close to 143B; towards the apex, tinged with close to 60A and 60B.

*Inflorescence height*.—About 20.1 cm.

*Inflorescence diameter*.—About 11.4 cm.

*Flower diameter*.—About 8 mm by 8 mm.

*Flower depth*.—About 7 mm.

*Petals*.—Quantity per flower: Typically five in a single whorl. Length: About 6 mm. Width: About 1 mm. Shape: Oblanceolate. Apex: Acute. Base: Narrowly cuneate. Margin: Entire; not undulate. Texture and luster, upper and lower surfaces: Smooth, glabrous; matte. Color: Developing petals, upper and lower surfaces: Close to 60D. Fully expanded petals, upper and lower surfaces: Close to 63B; venation, close to 63B; color becoming closer to N66D with subsequent development.

*Sepals*.—Quantity per flower: Typically five in a single whorl; towards the base forming a campanulate-shaped calyx. Length: About 2 mm. Width: About 1 mm. Shape: Ovate. Apex: Acute. Base: Cuneate, fused. Margin: Entire. Texture and luster, upper and lower surfaces: Smooth, glabrous; matte. Color: Developing sepals, upper and lower surfaces: Close to 75C; towards the apex, close to 58B. Fully developed sepals, upper and lower surfaces: Proximally, close to 156D; distally, close to 58C.

*Peduncles*.—Length: About 19.4 cm. Diameter: About 3 mm. Angle: Primary peduncles, mostly erect; secondary peduncles, about 50° from primary peduncle axis. Strength: Strong. Texture and luster: Moderately to densely pubescent; slightly glossy. Color: Close to 146C.

*Pedicels*.—Length: About 1 mm. Diameter: About 0.5 mm. Angle: About 45° from peduncle axis. Strength: Moderately strong. Texture and luster: Moderately pubescent; matte. Color: Close to 61C.

*Reproductive organs*.—Stamens: Quantity per flower: About ten. Filament length: About 4 mm. Filament color: Close to 59D. Anther shape: Broadly ovate; basifixed. Anther length: About 0.3 mm. Anther diameter: About 0.2 mm. Anther color: Close to N77D. Pollen amount: Scarce. Pollen color: Close to 156D. Pistils: Quantity per flower: Two. Pistil length: About 1.5 mm. Stigma diameter: About 0.1 mm. Stigma shape: Club-shaped. Stigma color: Close to 59D. Style length: About 1.3 mm. Style color: Close to 63C. Ovary color: Close to 63C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, high light conditions, and temperatures ranging from about −25° C. to about 35° C. and to be suitable for USDA Hardiness Zones 5 through 10.

It is claimed:

1. A new and distinct *Astilbe* plant named 'Philoselmo' as herein illustrated and described.

* * * * *